United States Patent [19]

Audousset et al.

[11] Patent Number: 5,529,584
[45] Date of Patent: Jun. 25, 1996

[54] COMPOSITION FOR THE OXIDATION DYEING OF KERATINOUS FIBRES, COMPRISING A PARA-PHENYLENEDIAMINE DERIVATIVE AND 2-METHYL-5-AMINOPHENOL, AND DYEING PROCESS USING SUCH A COMPOSITION

[75] Inventors: Marie-Pascale Audousset, Asnieres; Jean Cotteret, Verneuil S/Seine, both of France

[73] Assignee: L'Oreal, Paris, France

[21] Appl. No.: 361,676

[22] Filed: Dec. 22, 1994

[30] Foreign Application Priority Data

Jan. 24, 1994 [FR] France .................. 94 00703

[51] Int. Cl.⁶ ..................................... A61K 7/13
[52] U.S. Cl. .................... 8/412; 8/406; 8/408; 8/410; 8/416; 8/421
[58] Field of Search ................ 8/405, 406, 408, 8/410, 412, 416, 421

[56] References Cited

U.S. PATENT DOCUMENTS

| | | | |
|---|---|---|---|
| 4,152,112 | 5/1979 | Buqaut et al. | 8/10.2 |
| 4,311,478 | 1/1982 | Buqaut et al. | 8/407 |
| 4,840,639 | 6/1989 | Husemeyer et al. | 8/410 |
| 5,021,066 | 6/1991 | Aeby et al. | 8/412 |
| 5,137,538 | 8/1992 | Madrange et al. | 8/412 |
| 5,203,875 | 4/1993 | Tuloup et al. | 8/414 |

FOREIGN PATENT DOCUMENTS

| | | |
|---|---|---|
| 0007537 | 2/1980 | European Pat. Off. . |
| 0400330 | 12/1990 | European Pat. Off. . |
| 2364888 | 4/1978 | France . |
| 3627398 | 2/1988 | Germany . |
| 2239265 | 6/1991 | United Kingdom . |
| W09109587 | 7/1991 | WIPO . |

OTHER PUBLICATIONS

Patent Abstracts of Japan, vol. 4, No. 174 (C–033), Dec. 12, 1980, Abstract of JP 55–115,814, Lion Corp.

*Primary Examiner*—Paul Lieberman
*Assistant Examiner*—Caroline L. Dusheck
*Attorney, Agent, or Firm*—Finnegan, Henderson, Farabow, Garrett & Dunner

[57] ABSTRACT

A composition for the oxidation dyeing of keratinous fibers, in particular human keratinous fibers such as hair, comprising, in a medium suitable for dyeing, at least one 2-(β-hydroxyethyl)-para-phenylenediamine oxidation dye precursor and at least one 2-methyl-5-aminophenol coupling agent, and methods of dyeing keratinous fibers with said compositions.

17 Claims, No Drawings

COMPOSITION FOR THE OXIDATION DYEING OF KERATINOUS FIBRES, COMPRISING A PARA-PHENYLENEDIAMINE DERIVATIVE AND 2-METHYL-5-AMINOPHENOL, AND DYEING PROCESS USING SUCH A COMPOSITION

The present invention is directed to a composition for the oxidation dyeing of keratinous fibers, in particular human keratinous fibers such as hair, which composition comprises, in combination, at least 2-(β-hydroxyethyl)-para-phenylenediamine and 2-methyl-5-aminophenol. The present invention is also directed to the use of such a composition.

It is known to dye keratinous fibers, in particular human keratinous fibers such as hair, with dye compositions containing oxidation dye precursors, in particular ortho- or para-phenylenediamines, ortho- or para-aminophenols, generally referred to as "oxidation bases," and coupling agents, also referred to as coloration modifiers, more particularly meta-phenylenediamines, meta-aminophenols and meta-diphenols. These compositions enable the "background" colorations obtained with the products of condensation of the oxidation bases to be modified and to be enriched with glints.

In the field of oxidation dyeing of hair, oxidation dye precursors and coupling agents which are capable of generating, when they are combined, a red coloration which has satisfactory resistance to light, to washing, to inclement weather, to perspiration and to the various treatments to which hair may be subjected, are actively sought.

The dyes must also be the least selective possible with regard to the fiber to be dyed. The selectivity of a dye is referred to as the difference in uptake (i.e. in dyeing power) of the dye on the hair fiber, which depends on whether the hair has been sensitized, or "damaged," to a greater or lesser extent, either by a treatment, such as a bleaching or a permanent wave, or by atmospheric agents, especially in the case of the ends of the hair.

Hitherto, these colorations were obtained with dyes based on para-phenylenediamine. However, the use of para-phenylenediamine is currently being questioned for toxicological reasons.

After considerable research conducted in this direction, it has been discovered that it is possible to obtain new non-toxic dyes which generate colorations ranging from red to purple, and which are both intense and resistant, by combining 2-(β-hydroxyethyl)-para-phenylenediamine with 2-methyl-5aminophenol. This discovery forms the basis of the present invention.

The present invention is thus directed to a composition for the oxidation dyeing of keratinous fibers, in particular human keratinous fibers such as hair, comprising a medium suitable for dyeing, the medium containing at least one 2-(β-hydroxyethyl)-para-phenylenediamine oxidation dye precursor and/or at least one of the addition salts thereof, and, at least one 2-methyl-5-aminophenol coupling agent and/or at least one of the acid addition salts thereof; with the proviso that the oxidation dye composition is free of an additional oxidation dye precursor selected from 3-methyl-para-aminophenol, 2-methyl-para-aminophenol and 2-hydroxymethyl-para-aminophenol.

The present invention is also directed to a dyeing composition as defined above, which is a ready-to-use composition, and which further comprises an oxidizing agent and has a pH ranging from 3 to 11.

The present invention also contemplates a process for dyeing keratinous fibers, in particular human keratinous fibers, comprising the steps of:

(i) applying to the fibers the dyeing composition as defined above; and (ii) using an oxidizing agent, the oxidizing agent being applied to the fibers simultaneously with or subsequent to the dyeing composition, to develop the color of the dyeing composition in an acidic, neutral or alkaline medium. The oxidizing agent can be added only at the time of use to the dyeing composition or can be present in a separate composition (B) that is applied simultaneously or sequentially in a separate manner.

The present invention further contemplates a kit for the dyeing of keratinous fibers, in particular human keratinous fibers, comprising at least two compartments, one of the compartments containing a dyeing composition as defined above, and another of the compartments containing a composition (B) containing an oxidizing agent in a medium suitable for dyeing.

A further embodiment of the present invention includes a process for the dyeing of keratinous fibers, in particular human keratinous fibers, comprising the steps of:

(i) applying to the fibers a dyeing composition as defined above, the dyeing composition being obtained from a kit for dyeing keratinous fibers comprising at least two compartments, one of the compartments containing the dyeing composition as defined above and another of the compartments containing a composition (B) containing an oxidizing agent in a medium suitable for dyeing; and (ii) using the oxidizing agent and the suitable dyeing medium, the agent and the medium being applied to the fibers simultaneously with or subsequent to the dyeing composition to develop the color of the dyeing composition in the medium.

The composition and process of the present invention are used for the oxidation dyeing of keratinous fibers in general. The preferred form of keratinous fibers taught by this invention is human keratinous fibers, such as hair.

The new dyes obtained in accordance with the present invention make it possible to achieve intense colorations ranging from red to purple, which colorations are also non-toxic, nonselective and particularly resistant at the same time to light, to inclement weather, to perspiration and to the various treatments to which hair may be subjected. Most particularly, they are very resistant to shampoos. Other characteristics, aspects, aims and advantages of the invention will emerge more clearly upon reading the description and the examples which follow.

The acid salts which may be used according to the invention are preferably independently chosen from hydrochlorides, sulphates, hydrobromides and tartrates.

The concentration of the oxidation dye precursor or of an acid addition salt thereof preferably ranges from 0.01% to 10% by weight approximately relative to the total weight of the dye composition, and more preferably ranges from 0.05% to 5% by weight approximately.

The concentration of the 2-methyl-5-aminophenol or of an acid addition salt thereof preferably ranges from 0.005% to 3% by weight approximately relative to the total weight of the dye composition, and more preferably ranges from 0.05% to 2% by weight approximately.

The oxidizing agent is preferably chosen from hydrogen peroxide, urea peroxide, alkali metal bromates and persalts such as perborates and persulphates. It is more preferable to use hydrogen peroxide as an oxidizing agent.

Composition (A), which contains the combination of the dyes as described above, may have a pH which preferably ranges from 3 to 11. The pH may be adjusted to the desired value either by using basifying agents which are conventionally used for dyeing keratinous fibers, such as aqueous ammonia, alkali metal carbonates, alkanolamines such as, for example, mono-, di- and triethanolamines and the derivatives thereof, sodium hydroxide or potassium hydroxide, or the compounds of formula:

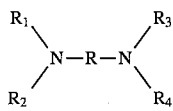

in which R is a propylene residue which is optionally substituted with a hydroxyl group or a $C_1$-$C_4$ alkyl radical; $R_1$, $R_2$, $R_3$ and $R_4$ represent, simultaneously or independently of each other, a hydrogen atom, a $C_1$-$C_4$ alkyl radical or a $C_1$-$C_4$ hydroxyalkyl radical; or by using standard acidifying agents, such as inorganic or organic acids, for example, hydrochloric acid, tartaric acid, citric acid and phosphoric acid.

The pH of the composition (B) containing the oxidizing agent as defined above is such that, after mixing with the composition (A), the pH of the composition applied to the keratinous fibers, preferably human keratinous fibers, preferably ranges from 3 to 11. The pH can be adjusted to the desired value using acidifying agents, or possibly basifying agents, which are well-known in the state of the art, such as those described above. The oxidizing composition (B) preferably comprises a solution of hydrogen peroxide.

According to a preferred embodiment of the dyeing process of the invention, the dye composition (A) described above is mixed, at the time of use, with an oxidizing solution in a sufficient amount to develop a coloration. The mixture obtained is then applied to the keratinous fibers, preferably human keratinous fibers, and is left to stand for preferably 5 to 40 minutes, and more preferably for 15 to 30 minutes, after which the fibers are rinsed, washed with shampoo, rinsed again and dried.

In addition to the dyes defined above, the dye compositions may also contain other direct dyes and/or coupling agents, especially in order to modify the shades or to enrich the shades with glints.

The dye compositions of the present invention may also contain antioxidants. The antioxidants may preferably be chosen from sodium sulphite, thioglycolic acid, thiolactic acid, sodium bisulphite, dehydroascorbic acid, hydroquinone, 2methylhydroquinone, tert-butylhydroquinone and homogentisic acid. and are generally present in proportions preferably ranging from approximately 0.05% to 1.5% by weight relative, to the total weight of the composition.

In another preferred embodiment, the dye compositions may also contain surface-active agents which are well-known in the art, in proportions preferably ranging from approximately 0.5% to 55% by weight, and more preferably ranging from 2% to 50% by weight, relative to the total weight of the composition; organic solvents in proportions preferably ranging from approximately 1% to 40% by weight, and more preferably from 5% to 30% by weight, relative to the total weight of the composition; or any other adjuvant which is cosmetically acceptable and is known in the prior art in the oxidation dyeing of hair.

The composition which is applied to the hair may preferably be provided in various forms, such as in the form of a liquid, a cream, a gel or any other form which is suitable for dyeing keratinous fibers and in particular human keratinous fibers such as hair. The composition may preferably be packaged under pressure in an aerosol can in the presence of a propellant and may be capable of forming a foam.

Concrete examples illustrating the invention will now be given. To begin with, a definition will be given of the tests used to evaluate the performance of the oxidation dyes according to the invention, regarding their resistance to perspiration, to light, to shampoos, to inclement weather or to permanent-waving.

Resistance to Perspiration:

A synthetic sweat solution of the following composition was used: 10 g of NaCl, 1 g of potassium hydrogen phosphate, 0.25 g of histidine, lactic acid to give pH=3.2 and distilled water to complete to 100 g.

The locks of dyed hair were immersed in the sweat solution which was contained in a crystallizing dish covered with a watch glass, and were left for a period of 20 to 50 hours at 37° C. The locks were then rinsed and dried.

Resistance to Light (Xenotest)

The dyed hair was attached to a support (cardboard or plastic). These supports were arranged on sample holders which rotated around a xenon lamp for a duration ranging from 20 to 80 hours, at a moisture content ranging from 25 to 75% RH (Relative Humidity) and at a temperature of 25° C.

Resistance to Shampoos (Ahiba-Texomat Machine)

Locks of dyed hair were placed in a basket which was immersed in a solution of a standard shampoo. The basket was subjected to an up-and-down movement of variable frequency and to a rotational movement, which reproduced the action of manual rubbing, thereby causing the formation of foam.

After a treatment time of 3 minutes, the locks were removed and then rinsed and dried. The dyed locks may have been subjected to several consecutive shampoo tests.

Resistance to Inclement Weather (Combined Test)

The dyed locks were exposed to strong light (Xenotest 40 h), at a relative humidity of 60%, and simultaneously, every 12 hours, and for a duration of 20 minutes, they were sprayed with water.

Resistance to Permanent-Waving

The dyed locks were immersed in a Dulcia Vital permanent-wave reducing solution (L'Oréal), of strength duration ranging from 1 to 3, for a duration ranging from 10 to 20 minutes; the locks were rinsed; they were then soaked in a fixing (oxidizing) solution for 5 minutes. After rinsing with water, washing with standard shampoo and rinsing with water, they were dried.

EXAMPLE 1

The following dye composition, in accordance with the invention, was prepared:

| | |
|---|---|
| 2-(β-Hydroxyethyl)-para-phenylenediamine dihydrochloride | 0.45 g |
| 2-Methyl-5-aminophenol | 0.40 g |
| Polyglycerolated oleyl alcohol containing 2 mol of glycerol | 4.0 g |
| Polyglycerolated oleyl alcohol containing 4 mol of glycerol (78% of AM) | 5.7 g AM |
| Oleic acid | 3.0 g |

| | |
|---|---|
| Oleyl amine containing 2 mol of ethylene oxide, sold under the name Ethomeen 012 by the company AKZO | 7.0 g |
| Diethylaminopropyl laurylaminosuccinamate sodium salt containing 55% of AM | 3.0 g AM |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite in aqueous solution containing 35% of AM | 0.4 g AM |
| Ammonium acetate | 0.8 g |
| Antioxidant, sequestering agent | qs |
| Fragrance, preserving agent | qs |
| Aqueous ammonia containing 20% of NH, | 10.0 g |
| Demineralized water qs | 100.0 g |

At the time of use, this composition was mixed weight-for-weight with 20 volumes of hydrogen peroxide (6% by weight), which had a pH of 3. A mixture having a pH of 9.8 was obtained.

This mixture was then applied to grey hair containing 90% white hairs, for 30 minutes. After rinsing, washing with shampoo, rinsing and drying, the inventors believe that the hair would be dyed a red-purple shade which would particularly resist shampoos remarkably well.

What is claimed is:

1. A composition for the oxidation dyeing of keratinous fibers, comprising a medium suitable for dyeing, said medium containing at least one oxidation dye precursor, wherein said oxidation dye precursor is 2-(β-hydroxyethyl)-para-phenylenediamine or an acid addition salt thereof; and at least one coupling agent, wherein said coupling agent is 2-methyl-5-aminophenol or an acid addition salt thereof; with the proviso that said composition is free of an additional oxidation dye precursor selected from 3-methyl-para-aminophenol, 2-methyl-para-aminophenol and 2-hydroxymethyl-para-aminophenol, wherein said at least one oxidation dye precursor and said at least one coupling agent are present in amounts effective to react with an oxidation agent to dye said keratinous fibers.

2. A dyeing composition according to claim 1, wherein said acid addition salt of said dye precursor and said acid addition salt of said coupling agent are independently selected from hydrochlorides, sulphates, hydrobromides and tartrates.

3. A dyeing composition according to claim 1, wherein said 2-(β-hydroxyethyl)-para-phenylenediamine or said acid addition salt thereof, is present in a concentration ranging from 0.01% to 10% by weight relative to the total weight of the composition, and said 2-methyl-5-aminophenol or said acid addition salt thereof, is present in a concentration ranging from 0.005% to 3% by weight relative to the total weight of the composition.

4. A dyeing composition according to claim 1, wherein said 2-(β-hydroxyethyl)-para-phenylenediamine or said acid addition salt thereof, is present in a concentration ranging from 0.05% to 5% by weight relative to the total weight of the composition, and said 2-methyl-5-aminophenol or said acid addition salt thereof, is present in a concentration ranging from 0.05% to 2% by weight relative to the total weight of the composition.

5. A dyeing composition according to claim 1, which is a ready-to-use composition, and which further comprises an oxidizing agent and has a pH ranging from 3 to 11.

6. A dyeing composition according to claim 1, wherein said keratinous fibers are human keratinous fibers.

7. A process for dyeing keratinous fibers to lower selectivity thereon, comprising the steps of:

(i) applying to said fibers to lower said selectivity the dyeing composition according to claim 1; and (ii) developing the color of said dyeing composition in an acidic, neutral or alkaline medium by applying an oxidizing agent to said fibers simultaneously with or subsequent to said dyeing composition.

8. A process according to claim 7, wherein said oxidizing agent is added to said dyeing composition at the time of applying in said step (i).

9. A process according to claim 7, wherein said oxidizing agent is separately contained in a composition (B) and is separately applied to said fibers simultaneously with said dyeing composition.

10. A process according to claim 7, wherein said oxidizing agent is separately contained in a composition (B) and separately applied to said fibers subsequent to said application of said dyeing composition.

11. A process according to claim 7, wherein said keratinous fibers are human keratinous fibers.

12. A kit for the dyeing of keratinous fibers comprising at least two compartments, one of said compartments containing a dyeing composition according to claim 1, and another of said compartments containing a composition (B) containing an oxidizing agent in a medium suitable for dyeing.

13. A kit according to claim 12, wherein said keratinous fibers are human keratinous fibers.

14. A process for dyeing keratinous fibers to lower selectivity thereon, comprising the steps of:

(i) applying to said fibers to lower said selectivity the dyeing composition according to claim 1; said dyeing composition being obtained from a kit for dyeing keratinous fibers comprising at least two compartments, one of said compartments containing said dyeing composition according to claim 1 and another of said compartments containing a composition (B) containing an oxidizing agent in a medium suitable for dyeing; and developing the color of said dyeing composition in said medium suitable for dyeing by applying said oxidizing agent to said fibers simultaneously with or subsequent to said dyeing composition.

15. A process according to claim 14, wherein said oxidizing agent is applied to said fibers simultaneously with said dyeing composition.

16. A process according to claim 14, wherein said oxidizing agent is applied to said fibers subsequent to said dyeing composition.

17. A process according to claim 14, wherein said keratinous fibers are human keratinous fibers.

* * * * *